United States Patent [19]

Bandurco et al.

[11] Patent Number: 4,672,116

[45] Date of Patent: Jun. 9, 1987

[54] SUBSTITUTED 5,6-DIALKOXYQUINAZOLINE DERIVATIVES

[75] Inventors: Victor T. Bandurco, Bridgewater, N.J.; Stanley C. Bell, Narberth, Pa.; John H. Dodd, Lebanon, N.J.; Robert Falotico, Belle Mead, N.J.; Charles F. Schwender, Califon, N.J.; Alfonso J. Tobia, Doylestown, Pa.

[73] Assignee: Ortho Pharmaceutical Corporation, Raritan, N.J.

[21] Appl. No.: 811,233

[22] Filed: Dec. 20, 1985

[51] Int. Cl.$^4$ .......................... C07D 239/80

[52] U.S. Cl. .................. 544/286; 544/116; 544/119; 544/250; 544/285; 544/287; 544/291; 544/292; 544/293

[58] Field of Search ............. 544/286, 285, 287, 291, 544/250, 116, 119, 292, 293

[56] References Cited

U.S. PATENT DOCUMENTS 4,351,832  9/1982  Rakhit et al. .................. 544/291

*Primary Examiner*—Glennon H. Hollrah
*Assistant Examiner*—James H. Turnipseed
*Attorney, Agent, or Firm*—Benjamin F. Lambert

[57] ABSTRACT

Quinazoline derivatives having an oxy substituent in 5 and 6 positions are described. The novel quinazoline derivatives are useful as cardiotonic agents.

8 Claims, No Drawings

SUBSTITUTED 5,6-DIALKOXYQUINAZOLINE DERIVATIVES

The present invention relates to novel quinazoline derivatives having an oxy substituent in the 5 and 6 positions. The novel compounds of the present invention have the following structural formulas:

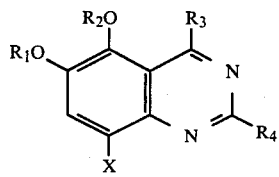

wherein $R_1$ and $R_2$ may be the same or different and are selected from hydrogen, loweralkyl wherein the alkyl group contains 1-6 carbon atoms; or when taken together $R_1$ and $R_2$ form a ring such as a methylenedioxy ring; X is hydrogen or halo; $R_3$ and $R_4$ are amino, lower alkoxy, wherein the alkoxy group contains 1-6 carbon atoms, alkylamino wherein the alkyl group contains 1-6 carbon atoms, dialkylamino wherein the alkyl group contains 1-4 carbon atoms, piperidino, piperazino, pyrrolidino, morpholino, cycloalkylamino such as, for example, cyclohexylamino, chloro, lower alkoxy amino wherein the alkoxy group contains 1-4 carbon atoms, hydroxylamino, hydrazino, alkylthio wherein the alkyl group contains 1-6 carbon atoms, hydroxy, and thiol; provided that when X is hydrogen $R_3$ is not hydroxy and $R_4$ is not amino or loweralkyl amino; and that $R_3$ and $R_4$ are not simultaneously hydroxy. Halo as used herein means fluoro, chloro, bromo or iodo and alkyl means straight or branched chain alkyl having 1-6 carbon atoms.

Quinazolines as a class have been reported in the literature and have been described as possessing antihypertensive activity. Some 5,6-dialkoxy 2(1H)quinozolines have been reported in U.S. Pat. No. 4,490,374 and in Ann. Chem. 730, 166 (1969). Unsubstituted 4-amino-2(1H)quinozolines have also been reported [M. Yamamoto, Chem. Pharm. Bull 26, 1633 (1978)] In addition, 5,6-dimethoxy-2-amino-4(3H)-quinazolinone is described as a synthetic intermediate in J. Med. Chem. 25, 703 (1982). Other alkoxy quinazolines have been reported in U.S. Pat. Nos. 3,833,587, 4,287,341 and 4,377,580 as well as in German Offenlegunschrift No. DE-2,258,403 and Chem. Pharm. Bull. 26, 1633 (1978).

The compounds of the present invention are substituted 5,6-dialkoxyquinazolines and possess positive inotropic activity. They are, therefore, useful in the treatment of heart failure.

The compounds of the present invention are prepared according to the following scheme:

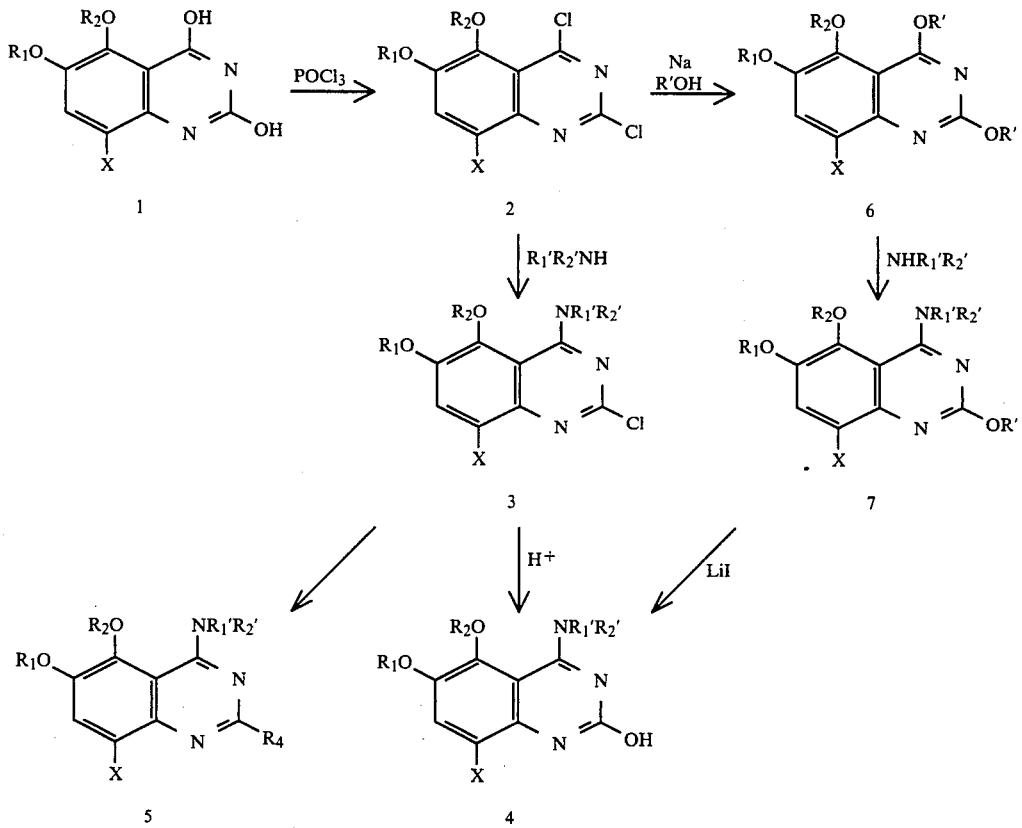

wherein $R'$ is lower alkyl having 1-4 carbon atoms or benzyl; $R_1'$ and $R_2'$ are hydrogen, lower alkyl having 1-4 carbon atoms or when taken together with nitrogen are piperidino, piperazino, pyrrolidino, morpholino, hydrazino, hydroxylamino, or cycloalkylamino and $R_1$, $R_2$, $R_4$ and X are as defined above.

As can be seen from the reaction scheme a 2,4-dihydroxyquinazoline (1) is first reacted with a halogenating agent such as phosphorus oxychloride in the presence of a base such as tripropylamine. The reaction is preferably carried out at the reflux temperature of the reaction mixture. The resultant 2,4-dichloro intermediate (2) is then reacted with ammonia or an appropriate amine such as, for example, methylamine, in a suitable solvent such as methanol to give the corresponding 4-methylamino-2-chloro-quinazoline (3). The 2-chloro compound (3) is then converted to the 2-hydroxy compound (4) by acid hydrolysis with a mineral acid such as, for example, dilute hydrochloric acid or is further displaced by a nucleophile such as an amine, hydrazine or alkoxide to give the corresponding substituted quinazoline (5).

Alternatively, the 2,4-dichloroquinazoline compound (2) is reacted with an alkoxide such as a sodium or potassium methoxide or benzyloxide in a solvent, such as, for example, dimethylformamide and tetrahydrofuran, to yield the 2,4-dialkoxy quinazoline (6). Reaction of the dialkoxy quinazoline (6) with an amine such as ammonia, methylamine, dimethylamine, piperidine or morpholine yields the 2-alkoxy-4-substituted amino quinazoline (7). The reaction is carried out in a suitable solvent such as, for example, methanol or ethanol. When the alkoxy group is a methoxy or benzyloxy group, the 2-alkoxy-4-amino quinazoline (7) can be converted to the 4-amino-2-hydroxy quinazoline (4) by reaction with sodium or lithium iodide in acetic acid. Similarly, the 2-methoxy- or 2-benzyloxy-4-substituted quinazolines can be converted to the 2-hydroxy-4-substituted quinazolines by reaction with sodium or lithium iodide in acetic acid.

Those compounds wherein $R_1$ or $R_2$ is hydrogen are prepared by conventional hydrolysis of the ether in the 5 or 6 position with, for example, hydrogen bromide.

Those compounds wherein $R_3$ or $R_4$ is alkoxyamino are prepared from the corresponding halogenated intermediate, such as the chloro intermediate, for example, by reaction with an appropriate alkoxyamine such as, for example, methoxyamine, ethoxyamine, propoxyamine and butoxyamine, in a suitable solvent such as ethanol, methanol, propanol, tetrahydrofuran, dioxane and dimethylformamide (DMF), for example. The reaction is preferably carried out at the reflux temperature of the solvent. Those compounds wherein $R_3$ or $R_4$ is a 2- or 4-thiol are prepared by reacting the 2- or 4-halo substituted quinazoline with thiourea in a suitable solvent such as ethanol, methanol, propanol and DMF. The reaction is preferably carried out at the reflux temperature of the solvent. Treatment of the thiourea with a dilute base such as sodium or potassium hydroxide, for example, results in the formation of the thiol analog, i.e., wherein $R_3$ or $R_4$ is SH. The lower alkylthio derivatives such as the methylthio or ethylthio compounds are prepared from the thiol derivatives by reaction with dimethyl sulfate or diethyl sulfate, for example, in a suitable solvent such as, for example, ethanol. The reaction is preferably carried out at the reflux temperature of the solvent. Alternatively, the alkylthio analogs can be prepared from the corresponding 2- or 4-halo intermediates by reaction of an alkylthiol such as methyl mercaptan or ethyl mercaptan, for example, in a suitable solvent such as dimethylformamide in the presence of a base such as sodium or potassium hydride.

The starting materials used in the preparation of the quinazoline derivatives, i.e., the substituted dihydroxy quinazolines, are prepared according to the methods described in copending application Ser. No. 653,620 filed Sept. 24, 1984, the pertinent subject matter of which is hereby incorporated by reference.

A second method of synthesis of 4-amino-2-hydroxyquinazolines involves the reduction of 5,6-dimethoxy-2-nitrobenzonitrile to the corresponding 2-amino intermediate. Reaction of the amino compound with potassium isocyanate followed by treatment of the N-(2-cyano-3,4-dimethoxyphenyl) urea with base gives the quinazoline product.

The intermediate urea can also be prepared by reaction of the 2-amino-5,6-dimethoxybenzonitrile with an alkylchloroformate such as ethyl chloroformate to form the urethane product. Reaction of the urethane with ammonia gives the above-mentioned urea.

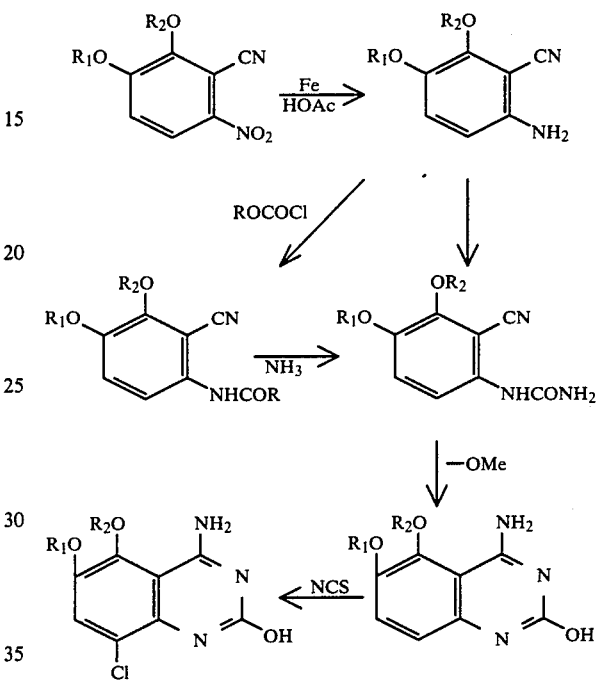

The 4-amino-2-hydroxyquinazolines can be converted to the corresponding 8-chloroquinazolines by reaction with N-chlorosuccinimide (NCS).

Also included among the compounds of this invention are the pharmaceutically acceptable acid addition salts prepared from organic and inorganic acids such as, for example, phosphoric acid, hydrochloric acid, hydrobromic acid, hypophosphoric acid, methanesulfonic acid, p-toluenesulfonic acid and sulfuric acid.

The novel quinazoline derivatives of this invention are active cardiotonic agents.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugar, diluents, granulating agents, lubricants, binders, disintegrating agents and the like in the case of oral solid preparations such as, for example, powders, capsules and tablets. Because of their ease in administration, tablets and capsules represent the most advantageous oral dosage unit form, in which case solid pharmaceutical carriers are obviously employed.

If desired, tablets may be sugar coated or enteric coated by standard techniques.

For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain per dosage unit, e.g., tablet, capsule, powder, injection, teaspoonful and the like, from about 0.01 to about 100 mg/kg of body weight and preferably from about 0.1 to about 20 mg/kg of the active ingredient.

The following examples describe the invention in greater particularity and are intended to be a way of illustrating but not limiting the invention.

EXAMPLE 1

4-Amino-8-chloro-5,6-dimethoxy-2-hydroxyquinazoline Monohydrochloride

A solution of 4-amino-2,8-dichloro-5,6-dimethoxyquinazoline (1.5 g, 0.0054 moles) and 6N hydrochloric acid (30 mL) was refluxed for 10 minutes. After cooling, the solid which precipitated was collected by filtration, washed with acetone and recrystallized from methanol. The resulting crystals were washed with methanol and dried under vacuum at 40° C. to afford the product (0.46 g), mp>300+ C.

When in the above procedure 4-amino-2-chloro-5,6-methylenedioxyquinazoline is substituted for 4-amino-2,8-dichloro-5,6-dimethoxyquinazoline the corresponding 4-amino-5,6-methylenedioxy-2-hydroxyquinazoline is obtained.

EXAMPLE 2

2,4,8-Trichloro-5,6-dimethoxyquinazoline

A mixture of 2,4-dihydroxy-5,6-dimethoxy-8-chloroquinazoline (3.0 g, 0.012 moles), phosphorus oxychloride (30 ml, 0.032 moles) and tripropylamine (3.56 g, 0.0249 moles) was mechanically stirred and refluxed for 16 hours. The excess phosphorus oxychloride was removed in vacuo and the resulting residue was added to ice/water (60 ml). The solid which resulted was immediately isolated by filtration, washed with water and recrystallized from isopropanol. The resulting crystals were washed with isopropanol and dried under vacuum at 45° C. to afford the product (2.43 g), mp 174°-175° C.

When in the above procedure 2,4-dihydroxy-5,6-methylenedioxyquinazoline is employed in place of 2,4-dihydroxy-5,6-dimethoxy-8-chloroquinazoline the corresponding 2,4-dichloro-5,6-methylenedioxyquinazoline is obtained.

EXAMPLE 3

2,8-Dichloro-4-hydroxy-5,6-dimethoxyquinazoline

A mixture of 2,4,8-trichloro-5,6-dimethoxyquinazoline (2.0 g, 0.0068 moles), sodium methoxide (0.367 g, 0.0068 moles) and methanol (100 ml) was stirred at reflux for 3 hours. The solvent was removed in vacuo and the residue was treated with water (50 ml), followed by acidification with glacidal acetic acid. The resulting aqueous mixture was extracted with dichloromethane (3×100 ml) and the combined organic extracts were dried over anhydrous sodium sulfate. After filtration and removal of solvent in vacuo the residue was recrystallized twice from methanol. The crystals were dried under vacuum at 40° C. to afford the product (0.168 g), mp 252°-253° C.

EXAMPLE 4

4-Amino-2,8-dichloro-5,6-dimethoxyquinazoline

A mixture of 2,4,8-trichloro-5,6-dimethoxyquinazoline (4 g, 0.013 moles) and saturated methanolic ammonia (60 ml) was warmed to 80° C. for 16 hours in a teflon lined, acid digestion bomb. The crude reaction mixture was filtered, and the resulting solid was recrystallized from N,N-dimethylformamide, washed two times with methanol and dried under vacuum at 60° C. to afford the product (3.26 g) mp>300° C.

When in the above procedure 2,4-dichloro-5,6-methylenedioxyquinazoline is employed in place of 2,4,8-trichloro-5,6-dimethoxyquinazoline the corresponding 4-amino-2-chloro-5,6-methylenedioxyquinazoline is obtained.

When, in the above procedure, methylamine or dimethylamine is employed in place of ammonia the corresponding 4-methylamino-2,8-dichloro-5,6-dimethoxyquinazoline and 4-dimethylamino-2,8-dichloro-5,6-dimethoxyquinazoline are obtained.

EXAMPLE 5

8-Chloro-2,4,5,6-tetramethoxyquinazoline

To a mechanically stirred solution of sodium methoxide (3.67 g, 0.068 moles) and methanol (200 ml), cooled to 0° C., was added 2,4,8-trichloro-5,6-dimethoxyquinazoline over a 10 minute period. The resulting suspension was stirred for 1 hour at 0° C. and then at reflux for 2.5 hours. The solvent was removed in vacuo and the residue was treated with water (200 ml), followed by acidification with glacial acetic acid. After stirring for 5 minutes, the aqueous mixture was extracted with dichloromethane (4×150 ml ) and the combined organic extracts were dried over anhydrous magnesium sulfate. The magnesium sulfate was removed by filtration and the solvent was removed in vacuo. The residue was recrystallized from methanol, washed with cold methanol and dried under vacuum at 45° C. to afford the product (1.07 g), mp 145°-146° C.

When, in the above procedure, sodium ethoxide is employed in place of sodium methoxide, the corresponding 8-chloro-2,4-diethoxy 5,6-dimethoxyquinazoline is obtained.

EXAMPLE 6

8-Chloro-4-hydrazino-2,5,6-trimethoxyquinazoline

A mixture of 8-chloro-2,4,5,6-tetramethoxyquinazoline (1.0 g, 0.0035 moles), anhydrous hydrazine (5 ml, 0.16 moles) and methanol (50 ml) was stirred at reflux for 0.5 hours. The solvent was removed in vacuo and the residue was recrystallized from methanol. The resulting crystals were washed with methanol (20 ml) and dried under vacuum at 50° C. to afford the product (0.665 g), mp 166°-168° C.

EXAMPLE 7

8-Chloro-2-ethoxy-4-hydroxy-5,6-dimethoxyquinazoline

A sodium ethoxide solution was prepared using sodium (2.50 g, 0.11 moles) and absolute ethanol (300 ml). To the above solution was added a suspension of 5,6-dimethoxy-2,4,8-trichloroquinazoline (3.0 g, 0.01 moles) in absolute ethanol (60 ml). The resultant suspension was refluxed for 2 hours. The solvent was removed in vacuo and the residue was treated with water (200 ml) followed by acidification with glacial acetic acid. The resulting aqueous mixture was extracted with dichloromethane (4×200 ml) and the combined organic extracts were dried over anhydrous magnesium sulfate. The magnesium sulfate was removed by filtration, followed by removal of solvent in vacuo. Recrystallization of the residue from ethanol (three times) followed by drying under vacuum at room temperature afforded the product (1.59 g), mp 210°–212° C.

EXAMPLE 8

8-Chloro-5,6-dimethoxy-2,4-dipiperidinylquinazoline

A solution of 8-chloro-2,4,5,6-tetramethoxyquinazoline (2.0 g, 0.0068 moles), piperidine (4.30 g, 0.0505 moles) and methanol (60 ml) was warmed to 80° C. for 16 hours in a teflon lined acid digestion bomb. The solvent was removed in vacuo and the residue was recrystallized three times from isopropanol. Further purification was accomplished by chromatography on silica gel (250 g) using diethyl ether as the eluant. After combining the enriched fractions and removing the solvent in vacuo. the residue was triturated with diethyl ether (10 ml). The resulting solid was filtered and dried under vacuum at room temperature to give the product (0.814 g), mp 154°–156° C.

When, in the above procedure, piperazine, pyrrolidine and morpholine are employed in place of piperidine the corresponding 8-chloro-5,6-dimethoxy-2,4-dipiperazinylquinazoline; 8-chloro-5,6-dimethoxy-2,4-dipyrrolidinoquinazoline and 8-chloro-5,6-dimethoxy-2,4-dimorpholinoquinazoline are obtained.

EXAMPLE 9

2,8-Dichloro-4-ethoxy-5,6-dimethoxyquinazoline Hemihydrate

A sodium ethoxide solution was prepared using sodium (0.60 g, 0.0025 moles) and absolute ethanol (200 ml). To this was added 2,4,8-trichloro-5,6-dimethoxyquinazoline (3.0 g, 0.010 moles). The resultant suspension was stirred for 1 hour at room temperature followed by cooling to 0° C. The resulting solid was isolated by filtration, recrystallized from ethanol and washed with ethanol (15 ml). After drying under vacuum at 40° C., the product was obtained (1.85 g), mp 145° C.–147° C.

When, in the above procedure, sodium methoxide is employed in place of sodium ethoxide the corresponding 2,8-dichloro-4-methoxy-5,6-dimethoxyquinazoline is obtained.

EXAMPLE 10

4-Amino-8-chloro-2-ethoxy-5,6-dimethoxquinazoline

A suspension of 4-amino-2,8-dichloro-5,6-dimethoxyquinazoline (1.5 g, 0.0054 moles) was stirred at reflux for 16 hours in a freshly prepared solution of sodium (0.25 g, 0.0108 moles) and ethanol (100 ml). The solvent was removed in vacuo and the residue was recrystallized from methanol. The product was isolated by filtration, washed with methanol (10 ml) and dried under vacuum at 50° C. to give the product (10.4 g), mp 180°–182° C.

EXAMPLE 11

4-Amino-8-chloro-2-hydrazino-5,6-dimethoxyquinazoline ¼ hydrate

A mixture of 4-amino-2,8-dichloro-5,6-dimethoxyquinazoline (1.5 g, 0.0054 moles), anhydrous hydrazine (5 ml, 0.16 moles) and methanol (100 ml) was heated at reflux for 8 hours and stirred at room temperature for 16 hours. The mixture was cooled to 0° C. and the precipitate which formed was collected by filtration. Recrystallization of the solid from methanol followed by drying under vacuum at 55° C. afforded the product (1.12 g), mp 168°–169° C.

EXAMPLE 12

8-Chloro-5,6-dimethoxy-4-methylamino-2-hydroxyquinazoline

A solution of 8-chloro-2,5,6-trimethoxy-4-methylaminoquinazoline (1.80 g, 0.0054 moles), sodium iodide (0.989 g, 0.0066 moles) and glacial acetic acid (50 ml) was refluxed for 8 minutes. The glacial acetic acid was removed in vacuo and the residue was diluted with water (100 ml). After extracting the aqueous solution with dichloromethane (2×25 ml) the combined organic extracts were dried over anhydrous magnesium sulfate, filtered and concentrated in vacuo. Recrystallization of the residue from ethyl acetate-isopropanol afforded the product (0.530 g), mp 219°–221° C.

EXAMPLE 13

8-Chloro-4-[2-(4-morpholino)ethylamino]-2,5,6-trimethoxyquinazoline

A mixture of 8-chloro-2,4,5,6-tetramethoxyquinazoline (2.5 g, 0.0091 moles), N-(2-aminoethyl)morpholine (5 ml) and methanol (60 ml) was refluxed for 3 hours. After removal of the solvent in vacuo, the residue was chromatographed on silica gel (100 g) using 20–50% ethylacetate-hexane as the eluant. The enriched fractions were evaporated in vacuo and the resulting product dried under vacuum at room temperature (0.365 g), mp 227°–228° C.

EXAMPLE 14

4-Amino-8-chloro-2,5,6-trimethoxyquinazoline

A mixture of 2,4,5,6-tetramethoxy-8-chloroquinazoline (2.1 g, 0.0073 moles) and saturated methanolic ammonia (60 ml) was warmed to 80° C. for 16 hours in a teflon lined acid digestion bomb. The crude reaction mixture was filtered, and the resulting solid was recrystallized twice from N,N-dimethylformamide, washed three times with methanol and dried under vacuum at 60° C. to afford the product (1.08 g), mp 203°–204° C.

EXAMPLE 15

2-Amino-5,6-dimethoxybenzonitrile

Iron powder (8.70 g, 156 mmol) was added to a suspension of (9.30 g, 44.5 mmol) of 2-nitro-5,6-dimethoxybenzonitrile in an acetic acid (30 ml) and 2-propanol (30 ml) mixture. The mildly exothermic reaction which resulted was allowed to reach 100° and a gentle reflux was maintained for 1 hour with application of heat. Charcoal (10 g) was added, the reaction mixture filtered, and the solid residue obtained was washed with hot 2-propanol (100 ml). The combined filtrates were evaporated to an oily residue which was redissolved in CHCl₃ and washed with 5% aqueous NaHCO₃ and saturated aqueous NaCl solution. The CHCl3 phase was dried with Na2SO4 and evaporated in vacuo to yield 7.0 g (88.4%) of the target compound as an oil.

EXAMPLE 16

Methyl 2-cyano-3,4-dimethoxyphenylcarbamate

Methyl chloroformate (18.6 g, 19.7 mmol) was added to a suspension of K2CO3 (2.71 g, 19.6 mmol) and 2-amino-5,6-dimethoxybenzonitrile (7.0 g, 39.3 mmol) in 70 ml of CHCl3. The resulting mixture was heated at reflux for 2 hours before using filtered and evaporated to a residual solid. Recrystallization of the crude material from MeOH yielded 4.64 g (50.2% of product in good purity.

EXAMPLE 17

2,3-Dimethoxy-6-nitrobenzaldehyde

A solution of 2,3-dimethoxy-6-nitrobenzaldehyde (15.0 g, 71.1 mmol) and hydroxylamine hydrochloride (6.42 g, 99.6 mmol) in formic acid was refluxed for 2 hours. The reaction was cooled to room temperature and poured into 1500 mL of ice water. The resulting suspension was made alkaline with solid KOH, then filtered, washed with water and air dried to yield the desired product.

EXAMPLE 18

1-(2-Cyano-3,4-dimethoxyphenyl)carbamate

K2CO3 (10.08 g, 72.955 mM) was added to a solution of 2-cyano-3,4-dimethoxy aniline (26.0 g, 145.91 mM) in CHCl3 (262.4 ml). Ethylchloroformate (69.7 ml, 79.16 g, 729.55 mM) was added and the mixture stirred mechanically at reflux temperature for 2 hours under N2. The reaction mixture was filtered, the solid washed with CHCl2 (525 ml) and the filtrate evaporated in vacuo to give 35.68 g of a brown solid, m.p. 96°-98° C.

EXAMPLE 19

1-(2-Cyano-3,4-dimethoxyphenyl)urea

A stream of dry ammonia gas was passed for 3 hours through a solution of ethyl-1-(2-cyano-3,4-dimethoxyphenyl)carbamate (2.0 g, 8 mM) and ammonium acetate (2.0 g) and the solution was maintained at 140° C. The light brown reaction mixture solidified after 1 hour. The resulting semi-solid was treated with ice-water to yield a white solid which was filtered, washed with water, isopropanol and then with ligth petroleum ether to afford the product as a white solid; 0.8 g (45.4%); m.p. 198°-200° C.

EXAMPLE 20

4-Amino-5,6-dimethoxy-2(1H)quinazoline 1-(2-Cyano-3,4-dimethoxyphenyl)urea (0.8 g, 3.6 mM) was refluxed for 2 hours with 21.8 ml of a 0.05N solution of sodium methodixe in absolute methanol. Absolute ethanol (150 ml) was added and the reaction mixture was then refluxed for an additional 22 hours. Removal of the solvents from the reaction mixture under vacuum gave a light brownish residue which was treated with water (15 ml). The suspension which formed was carefully neutralized with dilute acetic acid and the solid material was filtered, washed with cold water, and then with isopropanol, and dried to yield 0.55 g of a tan solid (67.0%); m.p. 268°-270° C.

The following compounds were made according to the procedures described above:

TABLE 1

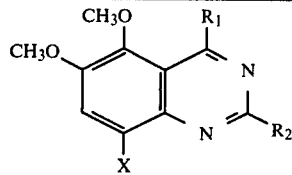

| Ex. | X | R1 | R2 | mp °C. |
|---|---|---|---|---|
| 21 | Cl | NHCH3 | Cl | 217-219 |
| 22 | Cl | NH—cyclohexyl | Cl | 187-188 |
| 23 | Cl | NHNH2 | Cl | >300 |
| 24 | Cl | OC2H5 | OC2H5 | 118-119 |
| 25 | Cl | N(CH3)2 | Cl | 137-139 |
| 26 | Cl | NHCH2CH2—N(morpholino) | Cl | 135-137 |
| 27 | Cl | NHCH3 | OCH3 | 110-112 |
| 28 | Cl | NHC3H7 | OH | 174-175 |
| 29 | Cl | NH—cyclohexyl | OH | 222-224 |
| 30 | 5-OH, 8-Cl | NHCH3 | OH | 280 dec. |
| 31 | Cl | OCH3 | OH | 193-195 |
| 32 | Cl | NHNH2 | OH | >400° dec. |
| 33 | Cl | NHOH | OH | 278-279° dec. |

The starting materials are prepared according to the following procedures:

PROCEDURE 1

2-Benzenesulfonyloxy-3-methoxybenzaldehyde o-Vanillin (350 g, 2.3 mols) was added to a solution of NaOH (166 g, 4.15 mols) in 2 l water. Benzenesulfonyl chloride (485 g, 2.74 mols) was added to the slurry at 20°-25° C. over 1 hour. The solid which formed was collected on a filter, washed with 2 l water, and redissolved in CH2Cl2. That solution was dried (MgSO4) and evaporated to a slurry. The solid was collected on a filter, the filtrate was further evaporated and filtered. The solid was washed with MeOH and dried in vacuo to afford the desired product, (511 g, 81.4%), mp 120°-122° C.

PROCEDURE 2

2-Benzenesulfonyloxy-3-methoxy-6-nitrobenzaldehyde

2-Benzenesulfonyl-3-methoxybenzaldehyde (250 g, 0.85 mols) was added to 90% HNO3 (2250 ml) with stirring at −2° C. over 10 minutes then stirred 5 minutes and poured over 8 kg of crushed ice. The solid which precipitated was filtered and washed with water. Both the solid and filtrate were extracted with CH2Cl2, the extracts were washed with aqueous K2CO3, dried (MgSO4) and evaporated with addition to MeOH to displace the CH2Cl2 to 400 ml, cooled, filtered and the solid washed with MeOH and dried in vacuo to afford (188 g, 65%) of aldehyde, mp 152°-155° C.

PROCEDURE 3

2-Benzenesulfonyloxy-3-methoxy-4-nitrobenzaldehyde

The filtrate from the above reaction contained the product of Procedure 3. Crystallization from methanol afforded 20% of the 4-nitrobenzaldehyde, mp 74°-76° C.

PROCEDURE 4

2-Hydroxy-3-methoxy-6-nitrobenzaldehyde

2-Benzenesulfonyloxy-3-methoxy-6-nitrobenzaldehye (115 g, 0.39 mols) was dissolved in 6 l MeOH and refluxed while a solution of KOH (68 g, 1 mol) in 145 ml $H_2O$ was added. The thick slurry was cooled to 30° C. and filtered. The collected solid was suspended in 1.5 l water and acidified with concentrated HCl (150 ml). The slurry was extracted with $CH_2Cl_2$, the extracts were dried ($MgSO_4$) and evaporated. The resulting solid was dissolved in MeOH (1.2 l) an evaporated to 500 ml. The crystals which formed were filtered and washed with MeOH to afford desired aldehyde, (20 g) mp 100°–101° C.

PROCEDURE 5

2-Hydroxy-3-methoxy-6-nitrobenzaldehyde potassium salt

Nitro benzenealdehyde from Procedure 4 (200 g) was dispersed in methanol (8 l) and heated to 60° C. A solution of KOH (127 g) in water (270 ml) was added over 30–60 minutes. The slurry was refluxed for 1 hour, cooled to 25°–30°, filtered and the solid washed with MeOH (1 l). The orange solid was dried in the vacuum oven to afford (132 g, 95%) of the desired product.

PROCEDURE 6

2,3-Dimethoxy-6-nitrobenzaldehyde

Potassium salt from Procedure 5 (396 g) was slurried with DMF (8 l) and added to a 1 l flask containing 800 g potassium carbonate. Dimethyl sulfate (420 ml) was added in portions at 60° over 1 hour and the reaction was stirred at 60° overnight. The $K_2CO_3$ was washed with acetone and the washings were added to the distillation residue and again solvent was removed in vacuo. The dry residue was treated with water (1 l) and extracted with $CH_2Cl_2$. The extracts were dried, evaporated, and the product was crystallized from methanol to afford the product, (335 g, 94%) mp 109°–111° C.

PROCEDURE 7

2,3-Dimethoxy-6-nitrobenzoic Acid 2,3-Dimethoxy-6-nitrobenzaldehyde from Procedure 6 (331 g) was added to acetone (2.5 l) in a 12 l flask. A saturated solution (approximately 60–65 g/l) of potassium permanganate was added until TLC showed no starting material. Approximately 7 l was required. The reaction mixture was filtered to remove the $MnO_2$ and was washed with 2.5N KOH and acetone (2 l each). The combined filtrates were evaporated to dryness and acidified with concentrated HCl. The precipitated solid was collected on a filter, washed with water (250 ml) and dried overnight. The solid was dissolved in 2 l acetone, treated with $MgSO_4$ and charcoal, evaporated to 500 ml and cooled to 5°. The crystals were filtered, washed with acetone and hexane and dried to afford dimethoxy acid (234 g, 65.7%) mp 187°–189° C.

PROCEDURE 8

2-Amino-5,6-dimethoxybenzoic Acid

A slurry of 2,3-dimethoxy-6-nitrobenzoic acid (5 g, 22 mM) in EtOH (200 ml) was treated with Pd/C (5%, 0.5 g) and the mixture hydrogenated in a Parr apparatus at 45 psi for 1 hour. The reaction mixture was filtered and the solvent removed from the filtrate. An off-white semi-solid residue was isolated. Crystallization from isopropanol afforded the amine, 3.8 g (86.7%), mp 71°–72° C.

PROCEDURE 9

2-Benzenesulfonyloxy-3-methoxy-4-aminobenzaldehyde

The 4-nitrobenzaldehyde from Procedure 3 (82.0 g, 243 mM) in glacial acetic acid (323 ml) and $H_2O$ (332 ml) at 90°–95° C. was treated with iron powder (103 g, 40 mesh) added in 10–12 portions during ¾ hour with vigorous stirring. When addition was complete the suspension was heated at 90°–95° C. for 3 hours. The reaction mixture was cooled and $H_2O$ (380 ml) added. The mixture is then filtered and the dark brown solid washed with EtOAc. Removal of solvent afforded 50 g of crude product. Crystallization from EtOAc and treatment with charcoal afford a yellow solid, 50 g (67%), mp 280°–282° C. dec.

PROCEDURE 10

2,4-Dihydroxy-5,6-dimethoxyquinazoline

2-Amino-5,6-dimethoxybenzoic acid (10.5 g, 53.2 mM) was dissolved in glacial acetic acid (100 ml) and potassium cyanate (10.8 g, 133.0 mM) in 120 ml $H_2O$ was added gradually and stirred for 2 hours at 60° C. After cooling the reaction mixture to 20° C., sodium hydroxide pellets (78.2 g, 196 mole) were added while maintaining the temperature below 60° C. The reaction mixture was then heated at 90° C. for 45 minutes. Upon cooling in an ice bath, the sodium salt of the product precipitated, was filtered, resuspended in $H_2O$ (120 ml), acidified (pH 3) with concentrated HCl, cooled, and filtered to give the crude product. Trituration with warm isopropanol afforded (60.8%) of a white solid, mp 266°–268° C.

PROCEDURE 11

2,4-Dihydroxy-5,6-dimethoxy-8-chloroquinazoline

A slurry of 2,4-dihydroxy-5,6-dimethoxyquinazoline (4.0 g, 18 mM) in $CHCl_3$ (1000 ml) was treated with N-chlorosuccinimide (4.6 g, 34.4 mM). The mixture was then refluxed with stirring for 18 hours. A light brown clear solution formed. It was cooled and subsequently washed with 10% aqueous sodium thiosulfate. The organic fraction was dried (anhyd. $MgSO_4$), filtered and the solvent remove in vacuo to give a brown solid. Trituration with isopropanol followed by warm methanol afforded the product as a light brownish solid; 2.4 g (52.2%); mp 282°–284° C.; $CDCl_3$ (TMS), $CF_3CO_2H$ 7.60 (s, 1H, 7—H), 4.15 (s, 3H, 5—$OCH_3$ or 6—$OCH_3$), 4.03 (s, 3H, 5—$OCH_3$ or 6—$OCH_3$); M+ 256.

The cardiotonic activity of the substituted quinazolines is determined according to the following general procedure:

Adult mongrel dogs are anesthetized with sodium pentobarbital (45 mg/kg, i.p.) and artificially respired. Arterial pressure (MAP) is recorded via a femoral artery and the pressure pulse is used to trigger a cardiotachometer for heart rate (HR). Left ventricular pressure is measured with a Millar catheter and $dP/dt_{max}$ is derived. A right thoracotomy is performed and cardiac output (CO) is determined by measuring ascending aortic blood flow with an electromagnetic flow probe. Myocardial contractile force (CF) is measured with a Walton Brodie strain gauge sutured to the right ventricle. A lead II EKG is also recorded. A standard does of dopamine is administered to determine myocardial responsiveness. The biological activity for some of the compounds of the present invention is set forth in Table 2. Compounds are administered by I.V. infusion and dose-related effects of the test compound on MAP, HR, $dP/dt_{max}$, CF and CO are expressed as a percent change from pretreatment control.

The cardiotonic activity of some representative compounds of this invention is tabulated below:

TABLE 2

![structure: CH3O, CH3O on benzene ring fused with N=C(R4)-N, R3 substituent, X substituent]

| X | -R₃ | R₄ | Cardiotonic Activity % inc. CF @ 1.87 mg/kg (iv) |
|---|---|---|---|
| H | NH₂ | OH | 221 |
| Cl | NH₂ | OH | 119 |
| Cl | OH | Cl | 5 |
| Cl | NH₂ | Cl | 6 |
| Cl | OCH₃ | OCH₃ | 9 |
| Cl | NH₂ | OCH₃ | 22 |
| Cl | OH | OC₂H₅ | 52 |
| Cl | OH | OC₃H₇i | 35 |
| Cl | OC₂H₅ | Cl | 11 |
| Cl | NHNH₂ | Cl | 16 |
| Cl | OC₂H₅ | OC₂H₅ | 4 |
| Cl | NHNH₂ | OCH₃ | 13 |
| Cl | NH₂ | OC₂H₅ | 69 |
| Cl | NHCH₃ | OH | 90 |
| Cl | NHC₃H₇ | OH | 93 |
| Cl | NH-phenyl | OH | 16 |
| Cl | OCH₃ | OH | 63 |
| Cl | NHOH | OH | 78 |

CF = Contractile Force

What is claimed is:

1. A compound of the formula:

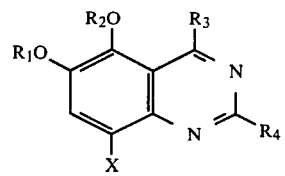

wherein R₁ and R₂ are the same or different and are selected from hydrogen, lower alkyl having 1–6 carbon atoms, or when taken together are methylene; X is hydrogen or halogen; R₃ and R₄ are amino, alkoxy having 1–6 carbon atoms, alkylamino having 1–6 carbon atoms, dialkylamine having 1–4 carbon atoms, piperidino, piperazino, pyrrolidino, morpholino, cyclohexylamino, chloro, alkoxyamino having 1–4 carbon atoms, hydroxylamino, alkylthio having 1–6 carbon atoms, hydroxy, hydrazino or thiol; and the pharmaceutically acceptable acid addition salts thereof provided that when X is hydrogen R₃ is not hydroxy and R₄ is not amino or alkylamino and that R₃ and R₄ are not hydroxy at the same time.

2. A compound of claim 1 wherein R₁ and R₂ are the same or different loweralkyl, X is halo and R₃ and R₄ are amino or hydroxy.

3. A compound of claim 1 selected from the group consisting of 2-hydroxy-4,5,6-trimethoxyquinazoline; 5,6-dimethoxy-2-hydroxy-4-methylaminoquinazoline; and their pharmaceutically acceptable acid addition salts.

4. A compound of claim 1 selected from the group consisting of 5,6-dimethoxy-2-hydroxy-4-hydroxyaminoquinazoline; 5,6-dimethoxy-2-hydroxy-4-hydrazinoquinazoline; 5,6-dimethoxy-2-hydroxy-4-propylaminoquinazoline; 2,4-dichloro-5,6-dimethoxyquinazoline; and 2,4,5,6-tetramethoxyquinazoline; and their pharmaceutically acceptable acid addition salts.

5. A compound of claim 1 selected from the group consisting of 4-amino-8-chloro-5,6-dimethoxy-2-hydroxyquinazoline; 8-chloro-5,6-dimethoxy-4-hydroxyamino-2-hydroxyquinazoline; 8-chloro-5,6-dimethoxy-2-hydroxy-4-methylaminoquinazoline; and 8-chloro-5,6-dimethoxy-2-hydroxy-4-propylaminoquinazoline; and their pharmaceutically acceptable acid addition salts.

6. A compound which is 4-amino-8-chloro-5,6-dimethoxy-2-hydroxyquinazoline.

7. A compound of claim 1 which is 4-amino-5,6-dimethoxy-2-hydroxyquinazoline.

8. A compound of claim 1 which is 4-methylamino-5,6-dimethoxy-2-hydroxyquinazoline.

* * * * *

UNITED STATES PATENT AND TRADEMARK OFFICE
CERTIFICATE OF CORRECTION

PATENT NO. : 4,672,116

DATED : June 9, 1987

INVENTOR(S) : Victor T. Bandurco et al.

It is certified that error appears in the above-identified patent and that said Letters Patent is hereby corrected as shown below:

Column 14, Claim 1, line 15, "dialkylamine" should read --dialkylamino--.

Signed and Sealed this

Third Day of November, 1987

Attest:

DONALD J. QUIGG

Attesting Officer

Commissioner of Patents and Trademarks